United States Patent [19]
Lardy et al.

[11] Patent Number: 6,153,606
[45] Date of Patent: Nov. 28, 2000

[54] MEMORY ENHANCEMENT BY THE ADMINISTRATION OF Δ5-ANDROSTENE-3β-OL-7,17-DIONE AND 3β ESTERS THEREOF

[75] Inventors: Henry A. Lardy; Jennifer Y. Shi, both of Madison, Wis.

[73] Assignee: Humanetics Corporation, Chanhassen, Minn.

[21] Appl. No.: 09/174,235

[22] Filed: Oct. 16, 1998

[51] Int. Cl.$^7$ ................................................. A61K 31/56
[52] U.S. Cl. ........................................... 514/177; 514/178
[58] Field of Search ..................................... 514/177, 178

[56] References Cited

U.S. PATENT DOCUMENTS

| | | | |
|---|---|---|---|
| 4,791,099 | 12/1988 | Aroonsakul | 514/2 |
| 4,812,447 | 3/1989 | Roberts | 514/170 |
| 5,292,730 | 3/1994 | Lardy, X . | |
| 5,296,481 | 3/1994 | Lardy IV . | |
| 5,424,463 | 6/1995 | Lardy, VII . | |
| 5,506,223 | 4/1996 | Lardy, XI . | |
| 5,556,847 | 9/1996 | Johnson et al. | 514/178 |
| 5,585,371 | 12/1996 | Lardy, VIII . | |
| 5,641,766 | 6/1997 | Lardy, II . | |
| 5,707,983 | 1/1998 | Lardy, III . | |
| 5,807,848 | 9/1998 | Lardy, IX . | |

FOREIGN PATENT DOCUMENTS

| | | | |
|---|---|---|---|
| 0 648 842 A2 | 4/1995 | European Pat. Off. | C12N 15/53 |
| 92 03 925 | 3/1992 | WIPO . | |
| WO 94/03176 | 2/1994 | WIPO | A61K 31/56 |
| 9403176 | 3/1994 | WIPO . | |
| 95 06 472 | 3/1995 | WIPO . | |
| WO 96/12810 | 5/1996 | WIPO | C12N 15/53 |
| WO 97/37664 | 10/1997 | WIPO | A61K 31/565 |

OTHER PUBLICATIONS

Shi, J. et al., "3β–Hydroxyandrost–5–ene–7,17–dione (7–Keto–DHEA) Improves Memory in Mice," *The FASEB Journal*, vol. 12, No. 5, Mar. 20, 1998, p. A764.

"Easing the Aches of Aging," *Star Tribune*, vol. XIII, No. 283, Thursday, Jan. 12, 1995, 1A, 13A.

"Humanetics Receives U.S. and Japanese Patents for the Use of 7–Keto DHEA to Mitigate the Effects of Alzheimer's," *Teltech Sentry Intelligence Service*, Mar. 25, 1998, p. 7.

"Humanetics to Sponsor Paper on 7–Keto DHEA to Augment Memory Function," *Teltech Sentry Intelligence Service*, Mar. 25, 1998, p. 6.

Akwa, Yvette et al., "Atrocytes and Neurosteriods: Metabolism of Pregnenolone and Dehydroepiandrosterone. Regulation by Cell Density," *The Journal of Cell Biology*, vol. 121, No. 1, Apr. 1993, pp. 135–143

Barrou, Zina et al., "Dehydroepiandrosterone (DHEA) and Aging," *Archives of Gerontology and Geriatrics*, vol. 24, No. 3, (1997), pp. 233–241.

Bologa, L. et al., "Dehydroepiandrosterone and Its Sulfated Derivative Reduce Neuronal Death and Enhance Astrocytic Differentiation in Brain Cultures," *Journal of Neuroscience Research*, vol. 17, (1987), pp. 225–234.

Brainum, Jerry, "DHEA The Mother of All Steroids," *IM*, Sep. 1996, pp. 101–107.

Danenburg, H. D., "Dehydroepiandrosterone (DHEA) Increases Production and Release of Alzheimer's Amyloid Precursor Protein," *Life Sciences*, vol. 59, No. 19, (1996), pp. 1651–1657.

Dubrovsky, B., "Natural Steroids Counteracting Some Actions of Putative Depressogenic Steroids on the Central Nervous System: Potential Therapeutic Benefits," *Medical Hypotheses*, vol. 49, (1997), pp. 51–55.

Flood, James F. et al., "Dehydroepiandrosterone and Its Sulfate Enhance Memory Retention in Mice," *Brain Research*, vol. 447, (1988), pp. 269–278.

Flood, James F. et al., "Dehydroepiandrosterone Sulfate Improves Memory in Aging Mice," *Brain Research*, vol. 488, (1988), pp. 178–181.

Flood, James F. et al., "Memory–Enhancing Effects in Male Mice of Pregnenolone and Steroids Metabolically Derived From It," *Proc. Natl. Acad. Sci.*, vol. 89, Mar. 1992, pp. 1567–1571.

Gorman, Christine, "Can This Pill Really Make Younger, "*Time*, Sep. 23, 1996, pp. 66–67.

Jaroff, Leon, "New Age Therapy" *Time*, Jan. 23, 1995, p. 52.

Maurice, Tangui et al., "Dehydroepiandrosterone Sulfate Attenuates Dizocilpine–Induced Learning Impairments in Mice via 1–Receptors", *Behavioral Brain Research*, vol. 83, No. 1 and 2, Feb. 1997, pp. 159–164.

Wolf, Oliver T. et al., "Effects of a Two–Week Physiological Dehydroepiandrosterone Substitution on Cognitive Performance and Well–Being in Healthy Elderly Women and Men," *Jjournal of Clinical Endocrinology and Metabolism*, vol. 82, No. 7, Jul. 1997, pp. 2363–2367.

McClain, Carla, "Anti-Aging Pill Shows Promise," *Tuscon Citizen*, pp. 1A, 10A.

McVicar, Nancy, "DHEA, Touted as Fountain of Youth, Still Has Its Share of Skeptics," *St. Paul Pioneer Press*, Tuesday, Dec. 3, 1996, pp. 1D, 2D.

Akwa, Yvette et al., "Neurosteroid Metabolism," *Biochem. Journal*, vol. 288, (1992), pp. 959–964.

Regelson, William et al., "Dehydroepiandrosterone (DHEA)–the Multifunctional Steroid," *Annals of the New York Academy of Sciences*, vol. 719, (1994), pp. 564–575.

Rosenberg, David R. et al., "Cognitive Enhancing Agents for the Treatment of Senile Dementia of the Alzheimer's Type," *Medicamentos de Actualidad*, vol. 26, No. 7, Oct./Nov. 1990, pp. 449–471.

(List continued on next page.)

*Primary Examiner*—Shep K. Rose
*Attorney, Agent, or Firm*—Knobbe, Martens, Olson & Bear, LLP

[57] ABSTRACT

The memory of a healthy mammal and the memory of a mammal with age impaired memory can be improved by administering an effective amount of Δ5-Androstene-3β-ol-7,17-dione and 3β esters thereof.

6 Claims, No Drawings

OTHER PUBLICATIONS

Shealy, C. Norman, "A Review of Dehydroepiandrosterone (DHEA)," *Integrative Physiological and Behavioral Science*, vol. 30, No. 4, Sep.–Dec. 1995, pp. 308–313.

Starka, Lubos et al., "7–Hydroxylation of Dehydroepiandrosterone by Rat–Liver Homogenate,"Biochimica et Biophysica Acta, vol. 56, (1962) pp. 76–82.

Sunderland, Trey et al., "Reduced Plasma Dehydroepiandrosterone Concentrations in Alzheimer's Disease," *The Lancet*, Sep. 2, 1989, p. 570.

Regelson, William et al., "Hormonal Intervention: "Buffer Hormones" or "State Dependency", " *Annals of the New York Academy of Science*, vol. 521, (1988), pp. 260–273.

Svec, Frank et al., "Antiglucocorticoid Actions of Dehydroepiandrosterone and Low Concentrations is Alzheimer's Disease," *The Lancet*, Dec. 2, 1989, pp. 1335–1336.

Wolf, Oliver T. et al., A Single Administration of Dehydroepiandrosterone Does Not Enhance Performance in Young Healthy Adults, but Immediately Reduces Cortisol Levels, *Biol. Psychiatry*, vol. 42, (1997), pp. 845–848.

Wolkowitz, Owen et al., "Dehydroepiandrosterone (DHEA) Treatment of Depression," *Biological Psychiatry*, vol. 41, No. 3, Feb. 1, 1997, pp. 311–318.

""DHEA" The Closet Thing to the Fountain of Youth," *Bio./Tech News*.

MEMORY ENHANCEMENT BY THE ADMINISTRATION OF Δ5-ANDROSTENE-3β-OL-7,17-DIONE AND 3β ESTERS THEREOF

FIELD OF THE INVENTION

The invention relates to the use of pharmaceuticals and dietary supplements to improve memory.

BACKGROUND

Mankind has sought ways to improve memory for years, including efforts ranging from the consumption of specific foods to meditation. While certain of these techniques have demonstrated limited success in improving memory, the search continues for alternative means for improving memory.

SUMMARY OF THE INVENTION

We have discovered that the memory of both a healthy mammal and a mammal with age impaired memory can be improved by administering an effective amount of Δ5-Androstene-3β-ol-7,17-dione and 3β esters thereof.

DETAILED DESCRIPTION OF THE INVENTION INCLUDING A BEST MODE

Definitions

As utilized herein, the term "healthy mammal" means a mammal having no diagnosed disease, disorder, infirmity, or ailment known to impair or otherwise diminish memory.

The Steroid

The steroid Δ5-androstene-3β-ol-7,17 dione is a derivative of dehydroepiandrosterone (DHEA) which does not appreciably stimulate, increase or otherwise enhance the production of sex hormones. The steroid is commercially available from a number of sources including Steraloids, Inc. of Newton, R.I. The 3β acetyl form of the steroid is commercially available from Humanetics Corporation of St. Louis Park, Minn. A number of procedures are available for synthesizing Δ5-androstene-3β-ol-7,17-dione and the 3β acetyl form from DHEA, with one such procedure described in U.S. Pat. No. 5,296,481.

Precursors of Δ5-androstene-3β-ol-7,17 dione may also be usefully employed for improving memory. Such precursors are readily metabolized in vivo to the active Δ5-androstene-3β-ol-7,17 dione. One example of such a metabolizable precursor is the commercially available Δ5-androstene3β-acetyl-7,17 dione. The 3β-acetyl group is hydrolyzed in vivo by esterases located in the blood and various tissues to produce the active Δ5-androstene-3β-ol-7,17 dione, and is believed to be less susceptible to oxidation during the manufacturing process than the hydroxy group found on the active Δ5-androstene-3β-ol-7,17 dione. Other metabolizable precursors include Δ5-androstene-3β, 17β-diol-7-one, Δ5-androstene-3β, 7α-diol-17-one, Δ5-androstene-3β, 7β-diol-17-one and the corresponding esters of these steroids.

Administration

Administration Route

The steroid can be administered by virtually any of the commonly accepted practices for the administration of pharmaceutical preparations including specifically, but not exclusively, mucosal administration, oral consumption, ocular administration, subcutaneous injection, transdermal administration, etc.

Mucosal administration of the steroid includes such routes as buccal, endotracheal, nasal, pharyngeal, rectal, sublingual, vaginal, etc. For administration through the buccal/sublingual/pharyngeal/endotracheal mucosa, the steroid may be formulated as an emulsion, gum, lozenge, spray, tablet or an inclusion complex such as cyclodextrin inclusion complexes. Nasal administration is conveniently conducted through the use of a sniffing power or nasal spray. For rectal and vaginal administration the steroid may be formulated as a cream, douch, enema or suppository.

Oral consumption of the steroid may be effected by incorporating the steroid into a food or drink, or formulating the steroid into a chewable or swallowable tablet.

Ocular administration may be effected by incorporating the steroid into a solution or suspension adapted for ocular application such as drops or sprays.

Subcutaneous administration involves incorporating the steroid into a pharmaceutically acceptable and injectable carrier.

For transdermal administration, the steroid may be conveniently incorporated into a lipophilic carrier and formulated as a topical creme or adhesive patch.

Dose Rate

The range of dosages and dose rates effective for achieving the desired biological properties and characteristics may be determined in accordance with standard industry practices. These ranges can be expected to differ depending upon whether the desired response is the prophylactic, modulatory, ameliorative or curative in nature.

EXPERIMENTAL

Experiment 1

(Aged Mice)

Aged, two year old mice were tested in the Morris water maze procedure by training the mice to locate the pedestal in less than 15 seconds in three consecutive trials. Immediately upon completion of training one group of mice was treated with DHEA (20 mg/kg) and a second group treated with an eqimolar amount of Δ5-Androstene-3β-acetyl-7,17-dione. Two weeks after treatment the time to rescue was timed in the Morris water maze procedure at: Control 36 seconds, DHEA 27 seconds, and Δ5-Androstene-3β-acetyl-7,17-dione 13 seconds.

Experiment 2

(Scopolamine-Induced Amnesia)

Groups of 13 to 16 C57BL76 mice (35 gm) were tested in the Morris water maze procedure by training the mice to locate the pedestal in less than 15 seconds in three consecutive trials. Immediately upon completion of training the mice in each of three groups were treated with scopolamine (1 mg/kg), scopolamine+DHEA, or scopolamine+Δ5-Androstene3β-acetyl-7,17-dione. Six days after treatment the average time (sec) to rescue was timed in the Morris water maze procedure at: Control 12.2±1.8; scopolamine 20.0±3.6; scopolamine+DHEA 9.7±1.6; and scopolamine+Δ5-Androstene-3β-acetyl-7,17-dione 8.3±1.8, wherein control vs. scopolamine $p</=0.055$; scopolamine vs. scopolamine+DHEA $p</=0.02$; and scopolamine vs. scopolamine+Δ5-Androstene-3β-acetyl-7,17-dione $p</=0.008$.

We claim:

1. A method for treating a mammal in need of improved memory, wherein said mammal has no diagnosed disease, disorder, infirmity or ailment known to impair or otherwise diminish memory, comprising the step of administering to the mammal an effective memory-improving amount of a steroid selected from the group consisting of Δ5-Androstene-3β-ol-7,17-dione and 3β esters thereof.

2. The method of claim 1 wherein the step of administering the steroid to a mammal comprises the step of administering the steroid to a human.

3. The method of claim 2 wherein the method improves the long term memory of the human.

4. The method of claim 2 wherein the step of administering the steroid comprises the step of injecting the steroid.

5. The method of claim 2 wherein the step of administering the steroid comprises the step of inducing ingestion of the steroid.

6. The method of claim 2 wherein the step of administering the steroid comprises the step of administering $\Delta$5-Androstene-3$\beta$-acetyl-7,17-dione.

* * * * *